United States Patent
Buttle et al.

(10) Patent No.: US 7,268,541 B2
(45) Date of Patent: Sep. 11, 2007

(54) DETECTING FAILURES OF FLEXIBLE MULTISTRAND STEEL STRUCTURES

(75) Inventors: David John Buttle, Wantage (GB); William Dalzell, Winchester (GB); Peter John Thayer, Oxford (GB); Stephen Frank Burch, Wantage (GB); Geoffrey Charles Eckold, Wantage (GB)

(73) Assignee: ESR Technology Limited, Warrington (GB)

( * ) Notice: Subject to any disclaimer, the term of this patent is extended or adjusted under 35 U.S.C. 154(b) by 0 days.

(21) Appl. No.: 10/562,148

(22) PCT Filed: Jun. 17, 2004

(86) PCT No.: PCT/GB2004/002590

§ 371 (c)(1), (2), (4) Date: Dec. 23, 2005

(87) PCT Pub. No.: WO2005/001466

PCT Pub. Date: Jan. 6, 2005

(65) Prior Publication Data

US 2006/0145693 A1  Jul. 6, 2006

(30) Foreign Application Priority Data

Jun. 25, 2003 (GB) .................................. 0314747.7

(51) Int. Cl.
*G01N 27/82* (2006.01)

(52) U.S. Cl. ..................................... 324/240; 324/228
(58) Field of Classification Search ................ 324/228, 324/239–240, 242–243
See application file for complete search history.

(56) References Cited

U.S. PATENT DOCUMENTS 5,414,353 A * 5/1995 Weischedel .................. 324/232
6,037,767 A   3/2000 Crescenzo .................. 324/220

FOREIGN PATENT DOCUMENTS

| EP | 0027368 | 4/1981 |
|---|---|---|
| EP | 0239537 | 9/1987 |
| GB | 2012966 | 8/1979 |
| GB | 2250097 | 5/1992 |
| WO | 02/06812 | 1/2002 |
| WO | 03/034054 | 4/2003 |

* cited by examiner

*Primary Examiner*—Bot LeDynh
(74) *Attorney, Agent, or Firm*—William H. Holt

(57) ABSTRACT

A flexible elongate structure, such as a flexible riser (10), comprising at least one layer (20) of steel wires near the surface which extend at least partly along the length of the structure, can be monitored by inducing a small, alternating magnetic field in the steel wires using an electromagnetic coil, and monitoring the magnetic flux density near the surface of the structure so as to asses the stress and hence detect if any wires have broken. By using an array of stress-measuring electromagnetic probes (24) around the structure some spatial resolution can be provided as to the location of any break in the wires.

6 Claims, 1 Drawing Sheet

DETECTING FAILURES OF FLEXIBLE MULTISTRAND STEEL STRUCTURES

This application is a 371 of PCT/GB04/02590 filed Jun. 17, 2004, which claims the foreign priority of United Kingdom application 03 104747.7 filed Jun. 25, 2003.

This invention relates to a method and apparatus for monitoring flexible multistrand steel structures such as cables or risers, for detecting failures.

Flexible risers are used to connect oil and gas wells to floating production platforms, the flexible riser being a steel-wire-reinforced flexible hose. Typically such a riser is connected to a turret on the floating platform, the turret providing some degree of rotation, and the flexible riser is typically hundreds of meters long. Failure in such a flexible riser can lead to significant quantities of oil leaking into the environment. It has been found that such risers typically fail close to the point at which the riser is connected to the turret, this failure being due to the fatigue loading endured by the riser at the point where the forces are greatest due to wave motion and rotation of the floating platform. This failure mode is recognised, but there exists no technology capable of inspection of such risers to warn of catastrophic failure, particularly with the flexible riser in situ connected to the turret and carrying a product.

According to the present invention there is provided a method for monitoring a flexible elongate structure comprising at least one layer of steel wires near the surface, the steel wires extending at least partly along the length of the structure, the method comprising inducing an alternating magnetic field much less than saturation in the steel wires using an electromagnetic coil, and monitoring the alternating magnetic flux density near the surface of the structure, determining from it a parameter indicative of stress in the steel wires, and hence detecting if any wires have broken.

Preferably the magnetic field is in a direction that is not parallel to the longitudinal axes of the wires. With some steels, in which longitudinal stress has a significant effect on the transverse magnetic permeability, the magnetic field is preferably in a direction perpendicular to the wires; with other steels the magnetic field is preferably in a direction between 30° and 60°, more preferably about 45°, to the direction of the wires.

Flexible risers include a helically-wound steel wire layer to provide tensile strength near the outer surface of the riser, and may in fact include two such steel wire layers. The failure mode typically involves fatigue fracture of one of the outer steel reinforcing wires or strands. When a wire fails in this way, the remaining intact wires or strands must take the extra load, and therefore their total stress increases. By arranging an array of electromagnetic stress sensing probes around the circumference of the riser the failure of one or more strands will result in a variation of the measured stress around the circumference. An increase in stress in one region indicates the failure of a strand in a nearby region, or at least an impending failure where a fatigue crack has propagated through a significant proportion of the cross-section of a strand or wire.

An alternative sensor arrangement is to use a single coil that encircles the elongate structure, so that changes in stress in all the reinforcing wires are monitored simultaneously. This may be preferable for smaller diameter risers, or for steel ropes and cables. Failure of one or more strands will lower the stresses in the failed strands but increase the stresses in the remaining intact strands, because the overall load is unchanged. However, because of the nonlinearity of the changes in magnetic properties of ferromagnetic materials with stress, the occurrence of such a failure can nevertheless be detected.

The preferred method utilises an array of electromagnetic stress sensing probes arranged around the circumference of the structure. This enables failure of a strand or wire to be detected, and also provides some spatial resolution as to the location of the failure. Greater resolution can be obtained by using smaller probes, but smaller probes are more affected by lift-off from the surface. A preferred arrangement uses probes that are of diameter between 30 mm and 90 mm, preferably about 60 mm, as such probes are not excessively affected by lift-off and nevertheless provide adequate spatial resolution. The optimum size depends on the size of the riser or cable.

In the preferred stress-measurement method the or each probe comprises an electromagnet means, means to generate an alternating magnetic field in the electromagnet means and consequently in the structure, and a magnetic sensor arranged to sense a magnetic field due to the electromagnet means; and the method comprises resolving signals from the magnetic sensor into an in-phase component and a quadrature component; deducing from the in-phase and quadrature components a stress-dependent parameter that is independent of lift-off; and deducing the stress from the stress-dependent parameter so determined.

This requires a preliminary calibration, with a specimen of the material, to determine how the in-phase and quadrature components of the signal vary with lift-off and with stress. The mapping may be represented in the impedance plane (i.e. on a graph of quadrature component against in-phase component) as two sets of contours representing signal variation with lift-off (for different values of stress) and signal variation with stress (for different values of lift-off), the contours of both sets being curved. Surprisingly it has been found that all the contours of constant stress can be represented by quadratic functions of the quadrature component; the coefficients of these functions are linearly related to a parameter, say D, which is independent of lift-off, and depends only upon the stress. Hence calibration measurements taken along no more than two different constant-stress contours (with known values of stress) enable the value of this parameter D to be calculated for any subsequent measurement, so the effect of lift-off can be eliminated.

Surprisingly this simple calculation has been found to provide a simple way to distinguish variations in material property (in particular, stress) from variations arising from lift-off or other geometrical variations such as surface texture or curvature.

Preferably the electromagnet means comprises an electromagnetic core and two spaced apart electromagnetic poles, and the magnetic sensor is preferably arranged to sense the reluctance (or flux-linkage) of that part of the magnetic circuit between the poles of the electromagnet means. The probe, or at least some of the probes, may also include a second magnetic sensor (a flux-leakage sensor) between the poles arranged to sense magnetic flux density parallel to the free space magnetic field. This second sensor detects flux leakage, which is influenced by changes in material properties, lift-off, and cracks.

The reluctance (or flux-linkage) signal from the or each probe is preferably backed-off, i.e. processed by first subtracting a signal equal to the signal from that sensor with the probe adjacent to a stress-free location. The backed-off signal is then amplified so the small changes due to stress are easier to detect. This backing off is performed after resolving into in-phase and quadrature components but before deducing the stress. Preferably the signals from the or each probe are digitized initially, and the backing-off and resolution are performed by analysis of the digital signals.

Whereas with the stress measurement system described in WO 03/034054 it is desirable to obtain measurements with each probe at a wide variety of different orientations, in the present context measurements at different orientations are not necessary since the stresses in the wires are almost exclusively along their length. A further complication in this case is that it is very difficult to obtain meaningful measurements by applying the magnetic field parallel to the direction of the wires, because this generates eddy currents which flow around the circumference of the individual wires, so that changes in magnetic permeability parallel to the wires are usually overwhelmed by the effect of these eddy currents. Hence there is unlikely to be any benefit from taking measurements at a range of different orientations of the magnetic field.

The invention will now be further and more particularly described, by way of example only, and with reference to the accompanying drawings, in which.

Figure 1:
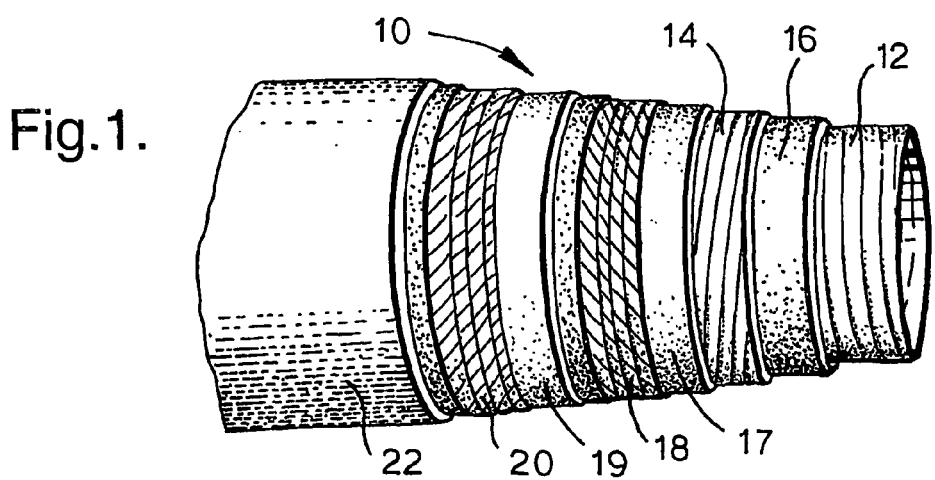
FIG. 1 shows a perspective cut-away view of part of a riser, to show its internal structure.

Referring to FIG. 1, a flexible riser 10, which acts as a hose to carry a pressurised fluid, has several concentric layers. An innermost layer 12 of helically wound bent steel strip provides resistance against external pressures, and a similar helically wound steel strip layer 14 provides hoop strength, and between these layers is a fluid barrier layer 16 of polymeric material. These are surrounded by two layers 18 and 20 of helically-wound steel strands to provide tensile strength, separated from the steel strip layer 14 and from each other by respective anti-wear layers 17 and 19. A polymeric layer 22 provides an external sleeve and fluid barrier. As discussed above, the failure mode with such a riser 10 is typically the failure of one or more strands in the outermost layer 20 of steel strands. But it will be appreciated that these strands cannot be observed directly, because they are enclosed within the outer layer 22.

Figure 2:
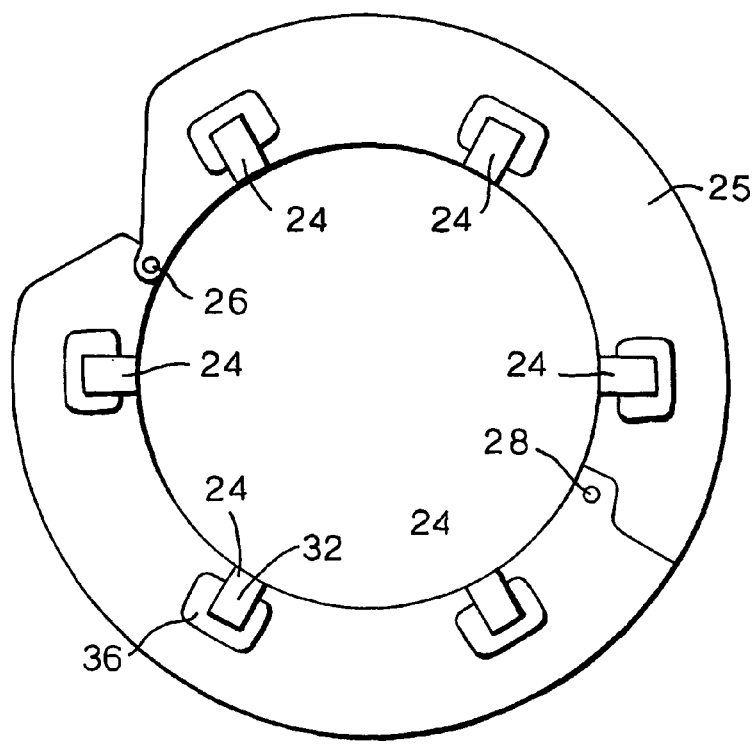
FIG. 2 shows an end view of a probe array for monitoring a riser as shown in FIG. 1, by making measurements of stress.

Referring now to FIG. 2, the stresses in the outermost layer 20 of steel strands of a riser 10 as shown in FIG. 1 may be monitored using an array of electromagnetic stress-measuring probes 24 in an annular frame 25. The frame 25 is in two generally semicircular halves which are hinged together at a pivot pin 26 and locked into an annular form by a securing pin 28. Hence in use the frame 25 can be clamped so as to surround the riser 10, there being a clearance of no more than 2 mm between the inside of the frame 25 and the outer surface of the riser 10. The frame 25 is shown as carrying only six electromagnetic probes 24, although it will be appreciated that it might support a different number, and indeed it would be preferable to have the separation between adjacent probes 24 similar to the width of each probe 24. (If probes are close to each other, they should not be energized at the same time.) If greater spatial resolution is required, there may be a second such array of probes 24 axially displaced and staggered in position relative to those shown.

Figure 3:
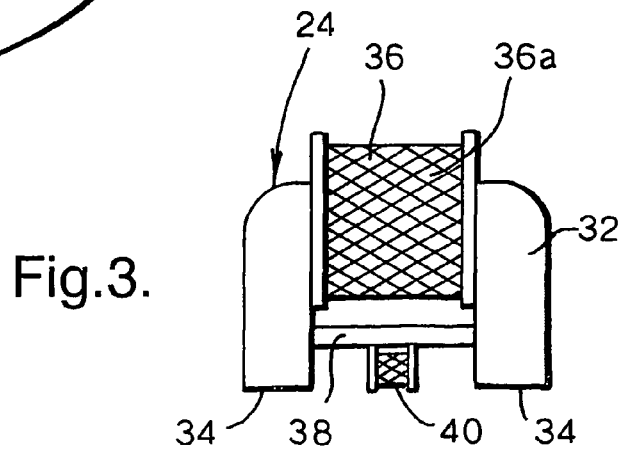
FIG. 3 shows a longitudinal sectional view of a probe for use in the array of FIG. 2.

Referring now to FIG. 3, each probe 24 includes a U-core 32 of silicon iron which defines two rectangular poles 34 in a common plane, each pole being 60 mm by 15 mm, and the space between the poles being 60 mm by 25 mm. The faces of the poles 34 are slightly curved to match the curvature of the outer surface of the riser 10. Around the upper end of the U-core 32 is a former on which are wound two superimposed coils 36 and 36a. One coil 36 has 250 turns, and in use is supplied with an AC current of 0.1 A, at a frequency of 70 Hz; this is the energising coil 36. When energized, this generates an alternating magnetic field in the U-core 32 and in the adjacent steel strands of the layer 20 in the riser 10, this magnetic field being small compared to the saturation field for the steel. The orientation of the probes 24 is such that the free space magnetic field is in a direction at 45° to the orientation of the steel strands in the layer 20. The other coil 36a is a sensing coil which provides the reluctance signals.

The probes 24 may also include other magnetic sensors, for example there may be a coil 40 between the poles whose longitudinal axis is parallel to the free-space magnetic field direction, supported on a non-magnetic plate 38 fixed between the arms of the U-core. This coil 40 detects leakage flux, and is significantly affected by lift-off. It may also be used to measure stress. The signals from the sensing coil 36a and from the leakage flux coil 40 (if provided) are amplified by a head amplifier before further processing. Another possible sensor is a flat coil between the poles whose longitudinal axis is normal to the surface of the riser 10; such a coil may be used in locating the strands if they are spaced apart.

In operation, with the probes 24 clamped around the riser 10, the alternating current is supplied to the drive coils 36. The in-phase and quadrature components of the flux linkage signal (i.e. the component in phase with the drive current, and the component differing in phase by 90°) received from the sensing coil 36a are each backed off to zero, and the backing off values are then fixed. During all subsequent measurements the flux linkage components are backed off by these same amounts (i.e. subtracting a signal equal to the component observed at a stress-free location or at any rate a location of uniform stress).

The value of the stress in the layer 20 in the longitudinal direction can be determined from the experimental measurements of flux linkage, once the measurements have been compensated for lift-off. This requires calibration of the probe 24, taking measurements on a sample of material of the same type as that of the steel strands 20, while subjecting it to a variety of different stresses. This may be done with a rectangular strip sample in a test rig, flux linkage measurements being made at the centre of the sample where the principal stress direction is aligned with the axis of the test rig.

As explained in WO 03/034054, the backed-off in-phase and quadrature components of the reluctance signal from the coil 36a can be plotted on a graph. A first set of measurements are made at progressively larger values of lift-off but with no stress. This gives a changing-lift-off contour. Similar lift-off contours can be obtained for other fixed values of stress. Measurements are then made a range of different fixed values of lift-off with varying stresses (both compression and tension), providing changing-stress contours. Such a graphical display enables changes in lift-off to be distinguished from changes in stress. Such a calibration should be carried out for at least one of the probes 24, adjacent to a sample of material of the same type as that of the steel wires 20.

Although such a graphical approach does enable changes due to lift-off to be readily distinguished from changes due to stress, it has been found that the effect of lift-off can alternatively be eliminated by a simple calculation. This requires calibration measurements to obtain two different lift-off contours as described above, at two different values of stress, say 0 and 200 MPa. It has been found that all the contours of constant stress for a particular type of steel can be represented (if the in-phase component is i and the quadrature component is q) by equations of the form:

$$i=aq^2+bq+c$$

in which the coefficients a, b and c each depend linearly on a parameter D which is independent of lift-off and dependent only on stress. If the values of D for the calibration stresses are set at 0 and 1, the parameter D for any intermediate position in the impedance plane represents what proportion it is of the way between one contour and the other. For example if a position has the value D=0.5, this indicates that it is half way between the two calibration contours. Hence calibration measurements taken along no more than two different constant-stress contours (with known values of stress) enable the value of this parameter D to be calculated for any subsequent measurement, so the effect of lift-off can be eliminated.

Thus this calculation method provides a stress-dependent parameter, D, that is independent of lift-off. It is also independent of amplifier gain and probe size, so that the calibration may be carried out with a smaller probe, if that is more convenient.

It will be also appreciated that in the present context it is unnecessary to calculate the stress in numerical terms (e.g. in MPa), as it is merely necessary to detect a position around the circumference of the riser 10 at which the measured value of stress in the strands is significantly less than at other positions. For example, if the graphical (contour) method is used to distinguish stress effects from lift-off, then the value of stress may be simply indicated by the magnitude of the reluctance signal at zero lift-off. And if the calculation method is used, the parameter D may be used as an indication of the stress.

In some instances it may be preferable to determine the actual value of the stress, e.g in MPa, particularly where knowledge of the magnitude of the stress in relation to the yield stress of the material is required in order to evaluate the integrity of the structure. This would be the case for example with a wire rope, if the risk of breaking is to be assessed.

With a riser 10, a break in a strand within the layer 20 locally reduces the stress in that strand to near zero and slightly increases the stresses in all the other strands. Over a length of several meters the resulting non-uniformities in stress are evened out, as the stresses are transmitted between adjacent strands. However, it has been found that such a break in a steel strand almost always occurs near an end of the riser 10 (within the connection to an end-fitting). Hence as long as the array of probes 24 is arranged to monitor stresses within a few meters of an end of the riser 10, the strand failure can be detected from the consequential stress differences. The measurements are preferably made no more than 0.5 m from the end-fitting, and more preferably no more than 0.2 m from the end-fitting.

The invention claimed is:

1. A method for monitoring a flexible elongate structure with a generally cylindrical surface, the structure comprising at least one layer of steel wires near the cylindrical surface, the steel wires extending at least partly along the length of the structure, the method comprising inducing an alternating magnetic field in the steel wires using at least one electromagnetic probe adjacent to the cylindrical surface of the structure, the or each probe incorporating an electromagnetic coil to induce the said alternating magnetic field, and monitoring the alternating magnetic flux density near the cylindrical surface of the structure in the vicinity of the said probe, determining from the monitored flux density a corresponding parameter indicative of stress in the steel wires, detecting a position at which the stress in the wires is significantly less than at other positions, and hence detecting if any wires have broken.

2. A method as claimed in claim 1 wherein the magnetic field is in a direction at a non-zero angle to the longitudinal axes of the wires.

3. A method as claimed in claim 1 wherein the magnetic flux monitoring means forms part of the probe.

4. A method as claimed in claim 3 wherein the measurements are made using an array of said electromagnetic probes around the circumference of the structure.

5. A method as claimed in claim 1 wherein the method comprises resolving signals from each magnetic monitoring means into an in-phase component and a quadrature component, and deducing from the in-phase and quadrature components a stress-dependent parameter that is independent of lift-off.

6. An apparatus for monitoring a flexible elongate structure with a generally cylindrical surface, the structure comprising at least one layer of steel wires near the cylindrical surface, the steel wires extending at least partly along the length of the structure, the apparatus comprising at least one electromagnetic probe adjacent to the cylindrical surface of the structure, the or each probe incorporating an electromagnetic coil to induce an alternating magnetic field in the steel wires, and means for monitoring the alternating magnetic flux density near the cylindrical surface of the structure in the vicinity of the said probe, and means for determining from the monitored flux density a corresponding parameter indicative of stress in the steel wires, and hence for detecting if any wires have broken.

* * * * *